United States Patent [19]
Norton et al.

[11] Patent Number: 5,976,556
[45] Date of Patent: Nov. 2, 1999

[54] COMBINATION OF ACID PROTEASE ENZYMES AND ACIDIC BUFFERS AND USES THEREOF

[75] Inventors: Scott J. Norton, Argyle; Michael A. Bishop, Dallas, both of Tex.; Glen S. Gillis, Darmouth, Canada

[73] Assignee: Active Organics, Inc., Lewisville, Tex.

[21] Appl. No.: 08/664,056

[22] Filed: Jun. 13, 1996

[51] Int. Cl.$^6$ ................................................. A61K 7/48
[52] U.S. Cl. .................. 424/401; 424/94.1; 424/94.2; 424/94.66; 514/557; 514/844; 514/845; 514/846; 514/847; 514/859; 514/861; 514/863; 514/864
[58] Field of Search .................. 424/401, 94.1, 424/94.2, 94.66; 514/557, 844–847, 859, 861, 863, 864

[56] References Cited

U.S. PATENT DOCUMENTS

| | | | |
|---|---|---|---|
| 4,105,783 | 8/1978 | Yu et al. | 424/283 |
| 4,363,815 | 12/1982 | Yu et al. | 424/274 |
| 5,431,913 | 7/1995 | Phillips | 424/401 |
| 5,516,517 | 5/1996 | Gardner | 424/401 |

FOREIGN PATENT DOCUMENTS 439288  10/1974  U.S.S.R. .

OTHER PUBLICATIONS

Greenberg and Winnick, 1941, Plant Proteases, Journal of Biological Science, vol. 135, pp. 761–787.
Burke, 1990, "Facial Wrinkles", Postgraduate Medicine 88(1):207–227.
Epstein, 1990, "House and Garden Plants", in *Irritant Contact Dermatitis* (Marcel Decker, Inc., New York) pp.127–165.
Food Chemicals CODEX, 1981, (National Academy Press, Washington, D.C.) pp.496–497.
Fruton, 1971, "Pepsin", in *The Enzymes*, vol. 3 (Academic Press, New York) pp.119–164.
Glazer and Smith, 1971, "Papain and Other Plant Sulfhydryl Proteolytic Enzymes", in *The Enzymes*, vol. 3 (Academic Press, New York) pp.501–546.
Morimoto et al., 1987, "Bromelain–Induced Edema in the Rat Paw and Effects of Drugs", Ensho 7(6):563–567.
Norris and Elam, 1940, "Preparation and Properties of Crystalline Salmon Pepsin", J. Biol. Chem. 134:443–454.

(List continued on next page.)

*Primary Examiner*—Jyothsna Venkat
*Attorney, Agent, or Firm*—Pennie & Edmonds LLP

[57] ABSTRACT

Novel compositions comprising one or more of an acid protease and an acidic buffer, the acidic buffer comprising an acid and a pharmaceutically or cosmetically acceptable carrier, vehicle or excipient, useful for treating or preventing abnormal biological conditions, diseases or disorders, and/or for improving the texture or appearance of the skin, and/or for enhancing epidermal exfoliation and/or for enhancing epidermal cell renewal and to methods for the use of the compositions. The acid protease comprises one or more proteolytic enzymes which exhibit proteolytic activity at pH values below that of the surface of the skin, i.e., approximately pH 5.5. The acidic buffer comprises inorganic and/or organic acids or mixtures thereof with a pharmaceutically or cosmetically acceptable carrier, vehicle or excipient. The buffer is capable of reducing the pH of the surface of the skin to less than pH 5.5 and is susceptible to neutralization by normal epidermal processes. Such types of abnormal biological conditions, diseases or disorders include skin atrophy, i.e., the thinning and/or general degradation of the dermis often characterized by a decrease in collagen and/or elastin as well as decreased number, size and doubling potential of fibroblast cells, and other maladies including, but are not limited to dry skin, severe dry skin, dandruff, acne, keratoses, psoriasis, eczema, skin flakiness, pruritus, age spots, lentigines, melasmas, wrinkles, warts, blemished skin, hyperpigmented skin, hyperkeratotic skin, inflammatory dermatoses, age-related skin changes and skin in need of cleansers.

41 Claims, 3 Drawing Sheets

OTHER PUBLICATIONS

Ohman and Vahlquist, 1994, "In Vivo Studies Concerning a pH Gradient in Human Stratum Corneum and Upper Epidermis", Acta Dermato–Venereol. 74(5):375–379.

*Remington's Pharmaceutical Sciences*, 1980, 16th ed. (Mack Publishing, Inc., Easton, PA.).

Rodeheaver, 1975, "Proteolytic Enzymes as Adjuncts to Antimicrobial Prophylaxis of Contaminated Wounds", Am. J. Surg. 129(5):537–544.

Smith, 1994, "Hydroxy Acids and Skin Aging", Cosmetics and Toiletries 109:41–48.

Van Scott and Yu, 1989, "Alpha Hydroxy Acids: Procedures for Use in Clinical Practice", Cutis 43:222–228.

Van Scott and Yu, 1984, "Hyperkeratinization, Corneocyte Cohesion, and Alpha Hydroxy Acids", J. Am. Acad. Dermatol. 11:867–879.

Wehr et al., 1986, "A Controlled Two–Center Study of Lactate 12 Percent Lotion and a Petrolatum–Based Creme in Patients with Xerosis", Cutis 37(3):205–209.

COMBINATION OF ACID PROTEASE ENZYMES AND ACIDIC BUFFERS AND USES THEREOF

1. FIELD OF THE INVENTION

This invention relates to novel compositions comprising one or more of an acid protease enzyme and an acidic buffer, the acidic buffer comprising an acid and a pharmaceutically or cosmetically acceptable carrier, useful for treating or preventing abnormal skin conditions, diseases or disorders, and/or for improving the texture or appearance of the skin, and/or for enhancing epidermal exfoliation, and/or for enhancing epidermal cell renewal and to methods for the use of the compositions.

2. BACKGROUND OF THE INVENTION

It is well founded that exfoliation of epidermal layers of human skin induces an increased rate of epidermal cell renewal (E. Phillips, 1995, U.S. Pat. No. 5,431,913; W. P. Smith, 1994, Cosmetics and Toiletries 109:41–8). The human epidermis consists of multiple layers of stratified squamous epithelial cells in a constant state of renewal. New cells are formed first in the basal layer, which is the most internal membrane of the epidermis. These cells are displaced by the production of yet newer cells and subsequently are transported to the external layer of the epidermis, the stratum corneum, where they usually are shed (exfoliated) every two to three weeks. The general health and appearance of human skin depends greatly upon the rate of this process.

Certain situations or conditions, such as aging or exposure to the environment, can disturb this normal process and can lead to a generally reduced rate of cell renewal as well as an increased degree of intercorneocyte cohesion (VanScott and Yu, 1984, J. Am. Acad. Dermatol. 11:867–79). Because the time required for a cellular layer to migrate from the basal layer to the stratum corneum increases with the subject's age, the rate of epidermal cell renewal decreases. It has been reported that in a typical twenty year old person, the cells in the outer layers of the epidermis turn over on the average, every two weeks, while cell turnover intervals of more mature skin can be as much as twice as long (E. Phillips, 1995, U.S. Pat. No. 5,431,913). The decrease in cell renewal rate due to aging can be exacerbated by environmental conditions such as exposure to solar radiation and other climatic conditions (K. E. Burke, 1990, Postgraduate Medicine 88(1):207–27). A decrease in the cell renewal rate increases the time cells in the outer layers of skin are exposed to environmental conditions and may lead to further and/or cumulative damage. Certain studies suggest that a decrease in epidermal cell turnover rates is associated with an increase in intercorneocyte cohesion (VanScott and Yu, 1989, Cutis 43:222–28).

The cells of the epidermal layer are held together by proteinaceous components such as hemidesmosomes, desmosomes, gap junctions, glycosaminoglycans, proteoglycans, and other components present in the skin all of which have the ability to bind to each other and to cellular components. This binding together of the epidermal cells is described as "intercorneocyte cohesion", and the degree of the cohesive strength involved is affected by such factors as hydration and pH. Increased intercorneocyte cohesion results in hyperkeratinization and is characterized by thick and often dry or scaly skin caused by the retention of epidermal cells. The balance that exists between cohesion and cell turnover rates is responsible for normal rejuvenation of young skin and imbalances of these factors can result in the aged, rough, and unattractive look of mature epidermal surfaces. The search for topically active components that balance cell renewal rates and intercorneocyte cohesion is prominent in dermatological research efforts today (VanScott and Yu, 1984, J. Am. Acad. Dermatol. 11:867–79).

Recent advances in this research area have provided a number of topically active acidic compounds which show promise in this regard (Yu et al., 1978, U.S. Pat. No. 4,105,783; Yu et al., 1982, U.S. Pat. No. 4,363,815). Long term treatments with these acidic compounds result in an increased rate of epidermal cell renewal. Those acidic components known to be epidermally active, such as low molecular weight hydroxy or keto acids and esters thereof, are well documented with respect to their effectiveness as keratolytic/desquamation agents. High concentrations of these acids (e.g., salicylic and glycolic acids), as well as other acids such as trichloroacetic acid, are known for their ability to cause destruction of tissue at the site of application (W. L. Epstein, 1990, in *Irritant Contact Dermatitis*, Jackson and Glodner, eds., Marcel Decker, Inc., New York and Basel, pp. 127–165; Remington's Pharmaceutical Sciences, A. Osol, ed., Sixteenth Ed., Mack Publishing, Inc., Easton, Pa., 1980). At lower concentrations, these acids have been shown to have the ability to loosen the dead cells in the keratin-rich stratum corneum and interrupt intercorneocyte cohesion thereby facilitating desquamation; this activity is called "keratolytic activity" (Remington's Pharmaceutical Sciences, A. Osol, ed., Sixteenth Ed., Mack Publishing, Inc., Easton, Pa., 1980; W. P. Smith, 1994, Cosmetics and Toiletries 109:41–8).

Most keratolytics are skin irritants, including those listed above. Although some keratolytics are promoted as being more efficient than others, a comparison of the therapeutic index of each of these acids shows little advantage of one over another. The "therapeutic index" is an accurate method of rating the efficiency of these components which takes into account the component's keratolytic efficiency as well as the levels of irritation at a given concentration. It has been shown that even low levels of these components (greater than 4% acid concentration) cause significant skin irritation. The use of even lower levels of these components reduces irritation but generally reduces keratolytic effectiveness. Furthermore, prolonged use of the acids reduces the efficiency of cell renewal induction (W. P. Smith, 1994, Cosmetics and Toiletries 109:41–8). These shortcomings point out the need for a methodology to enhance the keratolytic effectiveness of these acids at non-irritating concentrations.

The application of proteolytic enzymes in topical therapy has been used for some time for such things as scar removal from burn wounds and as an adjunct to anti-microbial therapy (G. Rodeheaver, 1975, Am. J. Surg. 129(5):537–544). These enzymes include those generally restricted to plant sources, such as papaya (papain), fig (ficin), and pineapple (bromelain). Cosmetic formulations containing extracts from these plants and promoted as enhancing the removal of outer epidermal layers by proteolytic action have been marketed commercially. Although the substrate specificity and spectrum of activity in relation to pH suggest that the proteolytic action of these formulations should result in keratolytic activity at the outer epidermal layers, applications of proteolytic enzymes previously used in topical therapy have not been without drawbacks.

Those enzymes (e.g., papain, bromelain, and ficin) currently used in cosmetic applications generally exhibit proteolytic activity over a broad pH range of pH 3–pH 9 (Glazer and Smith, 1971, in *The Enzymes*, Vol. 3, P. Boyer, ed., Academic Press, New York, pp. 501–546). It is probably the broad pH range of these plant-derived enzymes that is responsible for at least some of the problems associated with prolonged skin exposure. Human epidermal systems maintain a pH gradient within the stratified layers of the skin; the outer layers have been reported to exhibit an average pH of 5.5 (W. P. Smith, 1994, Cosmetics and Toiletries 109:41–48). The pH of successive layers of the epidermis increases with depth, reaching a final pH closer to the physiological range (about pH 7.4) at the dermal layer. Because the plant-derived enzymes mentioned above remain active across this pH gradient, there is no pH control over these plant enzyme activities when they are applied to the skin.

The degree of therapeutic activity received by topical application of proteolytic enzymes has been governed by the intrinsic catalytic characteristics of those enzymes. The wide range of proteolytic activity, in relation to pH, exhibited by the proteases discussed above (pH 3–9) allows for little or no control over proteolytic activity by product formulation (Glazer and Smith, 1971, in *The Enzymes*, Vol. 3, P. Boyer, ed., Academic Press, New York, pp. 501–546). The plants from which these enzymes have been obtained are known to cause irritant contact dermatitis with symptoms including itching, edema, and blistering. It has been postulated that these enzymes are the primary cause of those symptoms possibly due to excessive decreases in intercorneocyte cohesion (W. L. Epstein, 1990, in *Irritant Contact Dermatitis*, Jackson and Glodner, eds., Marcel Decker, Inc., New York and Basel, pp. 127–165). The enzymes currently used in cosmetic applications can exhibit substrate-dependent proteolytic activity throughout all layers of the epidermis. Uncontrolled proteolysis of epidermal proteins that serve to stabilize intercorneocyte cohesion could decrease this intercorneocyte cohesion excessively and cause subsequent irritation. Proteolytic attack at the basal layer of the epidermis, where cell renewal originates, could cause imbalances in the rate of epidermal cell renewal. Blistering and edema could be the result of uncontrolled proteolytic attack by this class of enzymes at the basal membrane. This possibility is supported by the fact that injection of these plant enzymes into the skin of mammals is known to cause edema in the skin (Morimoto et al., 1987, Ensho 7(6):563–567). This finding has been used to produce experimental edema in dermatological research. Furthermore, the symptoms of irritant contact dermatitis listed above are similar to those induced by the most effective concentrations of epidermally active acidic components currently used in topical applications. Therefore, a more controlled approach to proteolytic activity with respect to topical applications should produce a desirable result without these side effects.

Compositions containing a proteolytic enzyme, pepsin, and several acids have been reported for the dissolution of dense necrotic formations seen, for example, with third degree burns (Soviet Union Patent No. 439288, 1974). There is no indication that these compositions are useful in enhancing epidermal exfoliation or that these compositions are active only for limited time periods.

Citation or identification of any reference in the background of this application shall not be construed as an admission that such reference is available as prior art to the present invention.

3. SUMMARY OF THE INVENTION

The present invention provides novel pharmaceutical and/or cosmetic compositions for treating or preventing abnormal skin conditions, diseases or disorders, and/or for improving the texture or appearance of the skin, and/or for enhancing epidermal exfoliation, and/or for enhancing epidermal cell renewal. The compositions comprise one or more of an acid protease and an acidic buffer. For purposes of this invention, the acid protease is an enzyme which exhibits peptidyl hydrolase (proteolytic) activity below the average pH of the surface of the skin and is significantly inactive at a pH greater than the average pH of the surface of the skin, which is about pH 5.5 for humans (W. P. Smith, 1994, Cosmetics and Toiletries 109:41–8). For men the average pH of the surface of the skin is about pH 5.3 and for women it is about pH 6.0 (Ohman and Vahlquist, 1994, Acta Dermato-Venereol. 74(5):375–379). For purposes of this invention, the average pH of the surface of the skin which is about pH 5.5 includes, in addition to others, gender-specific variations, such that a pH of about 5.5 includes a range of about pH 5.3, the average pH of the surface of a man's skin, up to about pH 6.0, the average pH of the surface of a woman's skin. Preferably, at a pH greater than or equal to the average pH of the surface of the skin (approximately pH 5.3–6.0), the acid proteases useful in this invention exhibit less than about 10% of the enzymatic activity they exhibit at their respective optimal pHs below the average pH of the surface of the skin.

The acid protease can be in the apoenzyme, holoenzyme, isoenzyme, or zymogen form. The acid protease component of the composition can be present in an amount of about 0.001% to about 75.0% by weight of the final composition, preferably about 0.1% to about 50%, more preferably about 1% to about 5%. The protease(s) has a specific activity of about 1.0 to about 5,000 HUT units/mg as determined by the method, as modified, described in Food Chemicals CODEX, 3rd ed., (1981), pp. 496–497, National Academy Press, Washington, D.C., see infra, Section 5.1. Preferably the protease(s) has a specific activity of about 50 to about 3000 HUT units/mg, more preferably about 500 to about 1500 HUT units/mg.

The acidic buffer is a composition which when topically applied to the skin, temporarily lowers the pH of the surface of the skin to less than about pH 5.5 but not lower than about pH 1.0, preferably to between about pH 2.5 and about pH 4.5. The acidic buffer composition comprises at least one acid and a pharmaceutically or cosmetically acceptable carrier, vehicle or excipient. The acid component of the buffer can be an inorganic or an organic acid or mixtures thereof. The acidic buffer is susceptible to neutralization to the average pH of the surface of the skin over time by natural epidermal processes, such as perspiration. The time period required for neutralization, and subsequent inactivation of the protease, will depend on the formulation of the acidic buffer. For example, shorter time periods result if the acidic buffer contains a weak acid or a weak buffering agent to counteract the relative alkalinity of the epidermis; longer time periods result if a stronger acid is utilized or a stronger buffering agent is employed in the acidic buffer. The acid component of the acidic buffer of the composition can be an organic acid or an inorganic acid or mixtures thereof and can be present in an amount of about 0.001% to about 95.0% by weight of the final composition, preferably about 0.01% to about 25%, more preferably about 1.0% to about 5%.

Control of the time period required for the pH of the surface of the skin to return to a pH of about 5.5 after topical application of a composition of the present invention allows for control of the activity of the protease enzyme. It is through this control of proteolytic activity that the present invention overcomes the drawbacks and complications found in the prior art, such as itching, burning, blistering, etc., caused by broad pH spectrum proteolytic enzymes. The period of time it takes for the surface pH of the skin to return to about pH 5.5 is determined by a number of factors, including the type of skin condition, disease or disorder that is being treated and the sensitivity of the skin of the particular subject being treated. To avoid the drawbacks and complications found in the prior art, ideally, the period of time should not exceed about 4 hours for any individual application of a composition of the present invention, preferably the period of time is between about 5 minutes to about 4 hours, more preferably between about 30 minutes to about 2 hours, most preferably between about 30 minutes to about one hour.

It is to be pointed out that the pharmaceutical compositions of the present invention are those which, when administered to the skin, render a benefit or an effect of treating or preventing an abnormal biological condition, disease, or disorder. Benefits or effects of treating or preventing such abnormal condition, disease, or disorder are the reduction in severity or disappearance of the symptoms or cause of the abnormal condition, disease, or disorder. The reduction in severity or disappearance of the abnormal condition, disease, or disorder may be either in the short- or long-term. Such abnormal biological conditions, diseases, or disorders to be treated by administering a composition of the present invention include, but are not limited to, dry skin, severe dry skin, dandruff, acne, keratoses, eczema, skin flakiness, pruritus, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers, as well as the effects of skin atrophy and psoriasis.

It is to be further pointed out that the cosmetic compositions of the present invention are those which, when administered to the skin, improve the texture or appearance thereof or enhance epidermal exfoliation and/or epidermal cell renewal, without necessarily rendering a benefit or an effect of treating or preventing an abnormal biological condition, disease, or disorder. In this context, improving the texture or appearance of the skin or enhancing epidermal exfoliation and/or epidermal cell renewal is meant to encompass providing a natural-looking and/or natural-feeling coating over the skin so as to enhance the beauty and/or smoothness of the skin from its pre-treated state, or to mask unwanted symptoms of an abnormal biological condition, disease, or disorder. This can include providing a temporary moisturizing effect to the epidermis. Such abnormal biological conditions, or diseases include, but are not limited to dry skin, severe dry skin, dandruff, acne, keratoses, psoriasis, eczema, skin flakiness, pruritus, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers, as well as the effects of skin atrophy, and psoriasis.

In yet another embodiment, the invention encompasses methods for treating abnormal skin conditions, diseases, or disorders including but not limited to dry skin, severe dry skin, dandruff, acne, keratoses, psoriasis, eczema, skin flakiness, pruritus, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers. The method comprises topically administering to an area of a subject's skin having the condition, disease, or disorder an effective amount of a composition comprising an acid protease which is enzymatically active below about pH 5.5 and an acidic buffer which lowers the surface pH of the skin to below about pH 5.5 for a period of time effective for the treatment of the condition, disease, or disorder, the acidic buffer being subject to neutralization by normal epidermal processes.

In yet another embodiment, the present invention provides methods for the enhancement of epidermal exfoliation and/or epidermal cell renewal comprising topically administering to an area of a subject's skin an effective amount of a composition comprising an acid protease which is enzymatically active below about pH 5.5 and an acidic buffer which lowers the surface pH of the skin to below about pH 5.5 for a period of time effective for enhancing epidermal exfoliation and/or epidermal cell renewal, the acidic buffer being subject to neutralization by normal epidermal processes.

In another embodiment, the invention provides methods for improving the texture or appearance of the skin comprising topically administering to an area of a subject's skin an effective amount of a composition comprising an acid protease which is enzymatically active below about pH 5.5 and an acidic buffer which lowers the surface pH of the skin to below about pH 5.5 for a period of time effective to improve the texture or appearance of the skin, the acidic buffer being subject to neutralization by normal epidermal processes.

In a still further embodiment, the invention provides methods for regulating the effects of skin atrophy comprising administering to an area of a subject's skin an effective amount of a composition comprising an acid protease which is enzymatically active below about pH 5.5 and an acidic buffer which lowers the surface pH of the skin to below about pH 5.5 for a period of time effective for regulating the effects of skin atrophy, the acidic buffer being subject to neutralization by normal epidermal processes.

In a preferred embodiment for enhancing epidermal exfoliation and/or epidermal cell renewal, the composition comprises pepsin and lactic acid. In this preferred embodiment for enhancing epidermal exfoliation and/or cell renewal, the composition comprises about 1.0% by weight of pepsin having a specific activity of about 1000 HUT units/mg and about 3.0% by weight of lactic acid. In a another preferred embodiment for enhancing epidermal exfoliation and/or cell renewal, the composition comprises about 1.0% by weight of pepsin having a specific activity of about 1000 HUT units/mg and about 1.5% by weight of lactic acid. In yet another preferred embodiment the composition comprises 1.0% by weight of pepsin and 1.0% by weight phosphoric acid. In another preferred embodiment the composition comprises 1.0% by weight of pepsin and 3.0% by weight phosphoric acid.

The compositions and methods of the present invention surprisingly demonstrate pharmaceutical activity or cosmetic effects against skin disorders heretofore not achieved by acids, α-hydroxycarboxylic acids, salicylic acids or broad pH spectrum proteases by themselves.

3.1 Definitions

As used in the present invention the following terms are intended to encompass the following:

ACIDIC BUFFER: A composition comprising an acid and a pharmaceutically or cosmetically acceptable carrier, vehicle or excipient which when topically applied to the skin lowers the surface pH of the skin to below about pH 5.5 and is subject to neutralization by natural skin processes such that the natural skin processes, over time, return the pH of the skin's surface to normal, which is about pH 5.5. The acid component of the buffer can be either an inorganic acid or an organic acid or mixtures thereof.

ACID PROTEASE: An enzyme which exhibits peptidyl hydrolase (proteolytic) activity at a pH below the average normal pH of the skin's surface, which is about pH 5.5, and which is significantly inactive at a pH greater than or equal to such average normal skin surface pH, i.e., less than about 10% activity at about pH 5.5 or greater as compared to peak activity at pH less than about pH 5.5. The acid protease can be in the apoenzyme, holoenzyme, isoenzyme or zymogen form.

COSMETIC: A formulation to be administered to the skin which improves the texture or appearance thereof, without necessarily rendering a benefit or an effect of treating or preventing an abnormal biological condition or a disease. Such improvement includes providing a temporary moisturizing effect to the mammalian epidermis.

EFFECTIVE AMOUNT: An amount of composition sufficient to significantly induce a positive modification in the condition to be treated, but low enough to avoid serious side effects. The effective amount of the composition will vary with the particular condition being treated, the age and physical condition of the subject being treated, the severity of the condition, the duration of the treatment, the nature of concurrent therapy, the specific composition employed, the particular pharmaceutically-acceptable carrier or cosmetically-acceptable carrier utilized, and similar factors within the knowledge and expertise of those skilled in the art.

EPIDERMAL CELL RENEWAL: The process by which new skin cells are formed in the basal layer, are transported to the external layer, the stratum corneum, and subsequently are exfoliated and replaced by yet newer skin cells.

EXFOLIATION: The detachment and shedding of superficial cells of an epithelium or from any tissue surface.

PHARMACEUTICAL: A formulation to be administered to the skin which renders a benefit or an effect of treating or preventing an abnormal biological condition or a disease.

REGULATING SKIN ATROPHY: The preventing, retarding, arresting, treating, or reversing the process of atrophy in mammalian skin.

SKIN ATROPHY: The thinning and/or general degradation of the dermis layer of mammalian skin often characterized by a decrease in collagen and/or elastin as well as decreased number, size and doubling potential of fibroblast cells. Skin atrophy is a natural result of aging, but may be caused by either intrinsic or extrinsic factors such as natural chronoaging, photodamage, burns or chemical damage, or by exposure to pollutants or allergens, e.g., cigarette smoke. Skin atrophy is often an undesirable side effect resulting from treatment with α-hydroxycarboxylic acids or salicylic acids.

The present invention may be understood more fully by reference to the detailed description and illustrative examples which are intended to exemplify non-limiting embodiments of the invention.

4. BRIEF DESCRIPTION OF THE DRAWINGS

Figure 1:
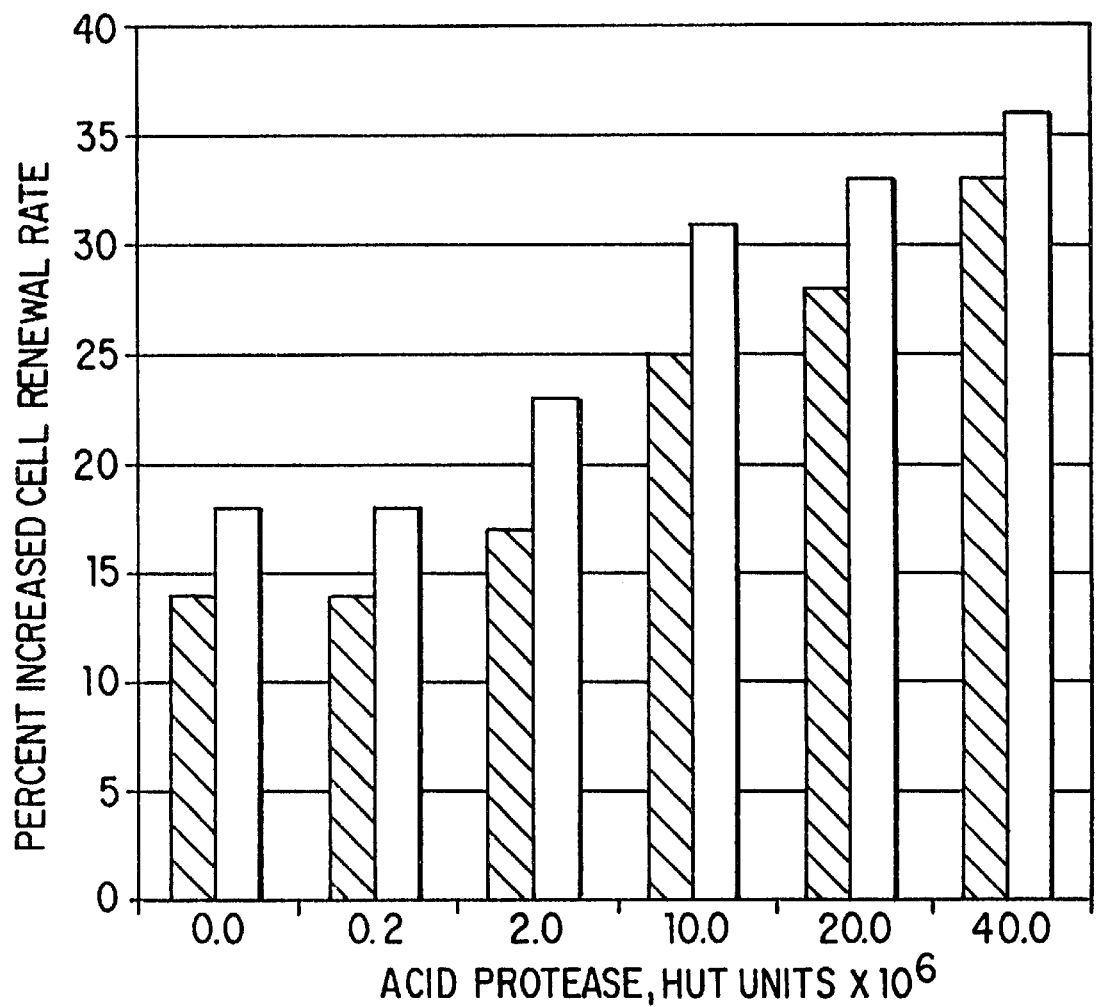
FIG. 1 is a bar graph demonstrating the effect on the rate of cell renewal with different concentrations of an acid protease (pepsin) with two different amounts of an acidic buffer (lactic acid). ▧ 1.5% lactic acid, □ 3.0% lactic acid.

5. DETAILED DESCRIPTION OF THE INVENTION 5.1 Compositions

The present invention provides novel compositions for treating or preventing abnormal skin conditions, diseases or disorders, and/or for improving the texture or appearance of the skin, and/or for enhancing epidermal exfoliation, and/or for enhancing epidermal cell renewal. The compositions comprise one or more of an acid protease and an acidic buffer. Such compositions are preferably to be administered topically, so as to minimize systemic effects or undesirable side effects. The inventor does not wish to be limited by a specific mode of action; however, the inventor believes that the compositions of the present invention accomplish the methods of the present invention by first lowering the pH of the surface of the skin to a value lower than the average pH of the skin, which is about 5.5 for humans. The reduction in pH allows for the activation of the acid protease component of the composition which exhibits proteolytic/keratolytic activity during the time that the skin's surface pH is below about 5.5. This time period depends upon the skin pH conditions of the individual and can be regulated by the formulation of the acidic buffer component. It is within the skill of the art to adjust the formulation so as to vary the time period and achieve the desired result.

During this time period, the acidic buffer is neutralized by natural epidermal processes, such as perspiration, such that the pH of the skin's surface returns to normal, which averages about pH 5.5. The increase in pH thus inactivates the acid protease and proteolytic/keratolytic activity ceases. The period of time in which the pH of the skin's surface is below about pH 5.5 and in which the protease component is active, is between about 1 minute to about 4 hours, preferably between about 30 minutes to about 2 hours, more preferably between about 30 minutes to about 1 hour.

For purposes of this invention, the acid protease is an enzyme which exhibits significant peptidyl hydrolase (proteolytic) activity below about pH 5.5, which is the average normal pH of the surface of the skin, and which is significantly inactive at a pH of about 5.5 or greater. For men the average pH of the surface of the skin is about pH 5.3 and for women it is about pH 6.0. For purposes of this invention, the average pH of the surface of the skin which is about pH 5.5 includes, in addition to others, gender-specific variations, such that a pH of about 5.5 includes a range of about pH 5.3, the average pH of the surface of a man's skin, up to about pH 6.0, the average pH of the surface of a woman's skin. The protease is significantly inactive when its activity is equal to or less than 10% activity as compared, for example, to its activity shortly after being applied to the skin as measured by the dansyl chloride test described in Section 6.1. Acid proteases useful in the present invention are those which, in an in vitro assay at pHs of about 5.5 and greater, display less than about 10% of the enzymatic activity measured in the same in vitro assay at the optimum pH (less than about pH 5.5) of the particular protease. See, e.g., Section 6.4, infra.

The acid protease can be in the apoenzyme, holoenzyme, isoenzyme, or zymogen form. Further, the acid proteases can be isolated from any source known to those of skill in the art, such as, for example, bacteria, fungi, tissue culture cells, and animals. The acid protease preparation can be present in an amount of about 0.001% to about 75.0% by weight of the final composition, preferably about 0.1% to about 50%, and most preferably about 1.0% to about 5.0%. The protease(s) will have a specific activity of about 1 to about 5000 HUT units/mg, preferably about 50 to about 3000 HUT units/mg, and most preferably about 500 to about 1500 HUT units/mg as determined by the method described in Food Chemicals CODEX, 3rd ed., (1981), pp. 496–497, National Academy Press, Washington, D.C., as modified described below.

Briefly, one first prepares the following stock solutions: HEMOGLOBIN SUBSTRATE is prepared by mixing 2 g bovine hemoglobin into 80 ml distilled water. The solution is then titrated to pH 2 by adding, for example, phosphoric acid and/or citric acid and additional distilled water is added for a total volume of 100 ml. This solution is separated into four equal portions and each portion is titrated to the desired pH with 50% sodium hydroxide or 50% hydrochloric acid. These final solutions are then heated at 30° C. for 20 minutes and are then filtered through glass wool. TCA STOCK is prepared by dissolving trichloroacetic acid in distilled water for a final concentration of 5% TCA.

Next, for each sample for which proteolytic activity is to be measured, prepare tubes labeled "B" and "T". In each tube place 4 ml of the hemoglobin solution and place at 37° C. such that the sample is prewarmed to 37° C. Into the "T" tube, add 100 $\mu$g enzyme solution, swirl gently and incubate at 37° C. for 20 minutes. Next add 10 ml TCA stock solution to each tube. Add an equal amount of the enzyme as above added to the "T" tube to the tube marked "B" which is the control for background absorbance. Centrifuge each tube and filter each sample through a syringe filter and place the filtered sample into a quartz cuvette for reading the absorbance at 280 nm. The actual absorbance is determined by subtracting the "T" sample's absorbance from the background. A standard curve can be generated by measuring known quantities of protease.

One HUT unit of proteolytic activity is defined as that amount of enzyme that produces, in one minute under the specified conditions of the assay, a hydrolysate whose absorbance at 280 nm is the same as that of a solution containing 1.10 $\mu$g per ml of tyrosine in 0.006 N hydrochloric acid. HUT units per gram are determined by the following formula:

$$HUT/g = (\text{absorbance at 280 nm} \times V)/(0.0084 \times T \times W)$$

where V is the final volume of the test solution, T is the reaction time in minutes, and W is the dry weight of the original enzyme sample used in the assay in grams. Protein concentration is determined by any method known in the art, such as, for example, the Bradford Assay which is described in Current Protocols in Molecular Biology, Ausubel et al., (Eds.), John Wiley & Sons, Inc., New York, 1994.

Examples of such proteases include, but are not limited to, pepsin, cathepsin, human urinary acid protease, fungal proteases derived from *Neurospora oryzae, Mucor pusillus, Mucor miehei, Rhizopus chinensis*, or *Endothia parasitica*, bacterial proteases rhizopuspepsin, penicillopepsin, and endothiapepsin. Further, the proteases may be derived from processes involving genetic engineering processes and techniques, whether involving embryonic, mature, or induced cells and products including DNA segments, plasmids, vectors, or expression thereof, or transformed cells, or pure cultures. It should be understood that two or more acid proteases can be used in combination such that the combined amount in weight percent is within the ranges mentioned above.

The acidic buffer is a composition which when topically applied to the skin, temporarily lowers the pH of the surface of the skin to less than about pH 5.5, but not lower than about pH 1.0, preferably about pH 2.5 to about pH 4.5. The acidic buffer composition comprises as least one acid and a pharmaceutically or cosmetically acceptable carrier, vehicle, or excipient. The acid component of the buffer is susceptible to neutralization to the average normal pH of the surface of the skin over time by natural epidermal processes, for example, by perspiration. The time period required for neutralization, and subsequent inactivation of the protease, will depend on the formulation of the acidic buffer. For example, shorter time periods result if the acid and/or buffering agent in the acidic buffer are weak relative to the neutralizing capacity of the epidermis; longer time periods result if a stronger acid is utilized or a stronger buffering agent is employed in the acidic buffer. The acid component of the acidic buffer of the composition can be an organic acid or an inorganic acid or mixtures thereof and can be present in an amount of about 0.001% to about 95.0% by weight of the final composition, preferably about 0.01% to about 25%, more preferably about 1.0% to about 5.0%. The weight % of the acid component will depend on acid strength and molarity. Moreover, the amount and strength of the acid component in the composition should be such that effective levels of proteolytic/keratolytic activity occurs but significant levels of skin irritation do not. Further, the acid component of the acidic buffer may or may not comprise an acid which has not been shown to exhibit any keratolytic activity but which merely provides an acidic environment for the activation of the protease. Examples of such acids include any molecule that can be manipulated in any composition to buffer the epidermal pH at pH ranges from about 0.1 to about 7 including, but are not limited to, lactic acid, sorbic acid, phosphoric acid, citric acid, glycolic acid, malic acid, gluconic acid, pyrophosphoric acid, triphosphoric acid, polyphosphoric acid, sodium bisulfate and potassium bisulfate. It should be understood that two or more acids can be used in combination such that the combined amount in weight percent is within the ranges mentioned above.

The acidic buffer also contains a component which is a pharmaceutically or cosmetically acceptable carrier, vehicle, or excipient. Examples of such pharmaceutically acceptable carriers, vehicles, or excipients are well known to those skilled in the art and can be found, for example, in *Remington's Pharmaceutical Sciences*, Eighteenth Edition, A. R. Gennaro, Ed., Mack Publishing Co., Easton, Pa., 1990. Examples of such cosmetically acceptable carriers or excipients are well known to those skilled in the art and can be found, for example, in *CTFA International Cosmetic Ingredient Dictionary*, Fourth Edition, J. M. Nikitakis, Ed., The Cosmetic, Toiletry, and Fragrance Association, Washington, D.C., 1991.

The compositions of the present invention intended for topical application may contain carrier, excipient, or vehicle ingredients such as, for example, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels, or ointments which are non-toxic and pharmaceutically, cosmetically, or dermatologically acceptable. Additionally, moisturizers or humectants can be added to the present compositions if desired. Examples of such additional ingredients useful for pharmaceutical compositions can be found in *Remington's Pharmaceutical Sciences*, Eighteenth Edition, A. R. Gennaro, Ed., Mack Publishing Co., Easton, Pa., 1990. Examples of such additional ingredients useful for cosmetic compositions can be found in *CTFA International Cosmetic Ingredient Dictionary*, Fourth Edition, J. M. Nikitakis, Ed., The Cosmetic, Toiletry, and Fragrance Association, Washington, D.C., 1991.

In addition to these and other vehicles which will be obvious to those of ordinary skill in the art, it will be understood that the pharmaceutical and cosmetic compositions of the present invention may include other ingredients such as, for example and not by way of limitation, those that improve or eradicate age spots, keratoses, and wrinkles; analgesics; anesthetics; antiacne agents; antibacterials; antiyeast agents; antifungal agents; antiviral agents; antidandruff agents; antidermatitis agents; antipruritic agents; antiemetics; antimotion sickness agents; antiinflammatory agents; antihyperkeratolytic agents; antidryskin agents; antiperspirants; antipsoriatic agents; antiseborrheic agents; hair conditioners and hair treatment agents; antiaging and antiwrinkle agents; antiasthmatic agents and bronchodilators; sunscreen agents; antihistamine agents; skin lightening agents; depigmenting agents; vitamins; corticosteroids; tanning agents; hormones; retinoids; topical cardiovascular agents; clotrimazole; ketoconazole; miconazole; griseofulvin; hydroxyzine; diphenhydramine; pramoxine; lidocaine; procaine; mepivacaine; monobenzone; erythidocaine; procaine; mepivacaine; monobenzone; erythromycin; tetracycline; clindamycin; meclocyline; hydroquinone; minocycline; naproxen; ibuprofen; theophylline; cromolyn; albuterol; retinoic acid; 13-cis retinoic acid; hydrocortisone; hydrocortisone 21-acetate; hydro-cortisone 17-valerate; hydrocortisone 17-butyrate; betamethasone valerate; betamethasone dipropionate; triamcinolone acetonide; fluocinonide; clobetasol propionate; benzoyl peroxide; crotamiton; propranolol; promethazine; vitamin A palmitate; vitamin E acetate hydrophilic thickening agents used in pharmaceutical formulations and mixtures thereof. Concentrations of these ingredients will vary depending upon intended use, e.g., therapeutic or cosmetic.

Control of the time period required for the pH of the surface of the skin to return to a normal pH of about 5.5 after topical application of a composition of the present invention allows for control of the activity of the protease enzyme. It is through this control of proteolytic activity that the present invention overcomes the drawbacks and complications found in the prior art, such as itching, burning, blistering, and other undesirable side effects caused by broad pH spectrum proteolytic enzymes. The determination of the period of time it takes for the surface of the skin to return to a normal pH of about pH 5.5 is determined by a number of factors, including the type of skin condition, disease, or disorder that is being treated, the type of skin and its location on the body, and the sensitivity of the skin of the particular subject being treated. To avoid the drawbacks and complications found in the prior art the period of time ideally should not exceed about 4 hours for any individual application of a composition of the present invention. The time limit will depend on a number of factors, such as the purpose of the application, for example, day to day maintenance, removal of rough dry skin, or therapeutic/pharmaceutical indications. Other factors include skin type, whether its sensitive, normal, insensitive, damaged or severely damaged and the mode of application, for example, a single application or a continuous wash or the spreading of a cream or lotion. Another factor is the protease itself since protease activity is substrate-dependent.

5.2 Methods of Use of the Compositions of the Present Invention

The present invention provides methods for enhancing epidermal exfoliation and/or for enhancing epidermal cell renewal. Such methods comprise topically administering to an area of a subject's skin an effective amount of a composition of the present invention, which comprises an acid protease enzyme exhibiting proteolytic activity below about pH 5.5 and insignificant activity at or above about pH 5.5 and an acidic buffer which lowers the pH of the surface of the skin to below about pH 5.5 for a period of time effective to enhance epidermal exfoliation and/or enhance epidermal cell renewal, the acidic buffer being subject to neutralization by natural epidermal processes.

The present invention also provides methods for improving the texture and/or appearance of skin. Such methods comprise administering to an area of a subject's skin an effective amount of a composition of the present invention, which comprises an acid protease enzyme exhibiting proteolytic activity below about pH 5.5 and insignificant activity at or above about pH 5.5 and an acidic buffer which lowers the pH of the surface of the skin to below about pH 5.5 for a period of time effective to improve the texture and/or appearance of skin, the acidic buffer being subject to neutralization by natural epidermal processes.

The present invention also provides methods for regulating the effects of skin atrophy. Such methods comprise administering to an area of a subject's skin an effective amount of a composition of the present invention, which comprises an acid protease enzyme exhibiting proteolytic activity below about pH 5.5 and insignificant activity at or above about pH 5.5 and an acidic buffer which lowers the pH of the surface of the skin to below pH 5.5 for a period of time effective to regulate the effects of skin atrophy, the acidic buffer being subject to neutralization by natural epidermal processes.

The present invention also provides methods for treating or preventing an abnormal skin condition, disease, or disorder. Such methods comprise administering to an area of a subject's skin an effective amount of a composition of the present invention, which comprises an acid protease enzyme exhibiting proteolytic activity below about pH 5.5 and insignificant activity at or above about pH 5.5 and an acidic buffer which lowers the pH of the surface of the skin to below pH 5.5 for a period of time effective to treat or prevent an abnormal skin condition, disease, or disorder, the acidic buffer being subject to neutralization by natural epidermal processes. Such condition, disease, or disorder includes, but is not limited to, dry skin, severe dry skin, dandruff, acne, keratoses, eczema, skin flakiness, pruritus, age spots, lentigines, melasmas, wrinkles (both coarse and fine, caused by intrinsic as well as extrinsic damage), blemished skin, hyperpigmented skin, hyperkeratotic skin, inflammatory dermatoses, age-related skin changes, skin in need of cleansers, and the effects of skin atrophy and psoriasis.

A preferred method of administering an effective amount of a composition of the present invention for any of the methods described above on an area of skin is via topical application. The amount of the acidic buffer and acid protease in the final composition and frequency of topical application to the skin can vary widely, depending upon factors such as the particular skin disorder, the severity of the skin disorder, the location and/or type of the skin involved, the subject's skin sensitivity, and the degree of treatment desired. It is well within the purview of the skilled artisan to regulate dosages according to the subject's need. It is suggested as an example that topical application range from about once per week to about 4 or 5 times daily, preferably from about 3 times a week to about 3 times daily, most preferably about once or twice per day. The final composition for topical application will comprise from about 0.001% to about 95%, preferably from about 0.01% to about 25%, most preferably from about 0.01% to about 5% of the acid component. The final composition for topical application will comprise from about 0.001% to about 75%, preferably from about 0.1% to about 50%, most preferably from about 1.0% to about 5% of the acid protease component. Another preferred mode of administering is chronic administration. "Chronic" administration, as used herein, means that the period of topical application may be over the subject's lifetime, preferably for a period of at least about one month, more preferably from about three months to about twenty years, more preferably from about six months to about ten years, more preferably still from about one year to about five years, thereby resulting in the treatment or prevention of the abnormal skin condition, disease, or disorder or in the improvement of the texture or appearance of the skin, or in the enhancement of epidermal exfoliation and/or epidermal cell renewal or the regulation of the effects of skin atrophy.

In another embodiment of the invention, the methods described above involve administering both an effective amount of the composition comprising an acidic buffer and an acid protease and an effective amount of one or more of a sunscreening agent, an anti-inflammatory agent, an antioxidant/radical scavenging agent, a chelating agent, a retinoid, self-tanning material, and/or a benzofuran derivative to the skin simultaneously. As used herein, "simultaneous application" or "simultaneously" means administering the agents to the skin at the same situs on the body at about the same time. Although this can be accomplished by administering the agents separately to the skin, preferably a composition comprising all the desired agents commingled is administered to the skin. The amount of sunscreening agent administered generally ranges from about 0.02 mg to about 1.0 mg per $cm^2$ skin. The amount of anti-inflammatory agent administered generally ranges from about 0.005 mg to about 0.5 mg, preferably from about 0.01 mg to about 0.1 mg per $cm^2$ skin. The amount of chelating agent administered generally ranges from about 0.001 mg to about 1.0 mg, preferably from about 0.01 mg to about 0.5 mg, more preferably from about 0.05 mg to about 0.1 mg per $cm^2$ skin. The amount of retinoid administered generally ranges from about 0.00001 mg to about 0.02 mg per $cm^2$ skin. The amount of benzofuran derivative administered generally ranges from about 0.001 mg to about 1.0 $mg/cm^2$ skin per application, preferably from about 0.01 to about 0.5 $mg/cm^2$ skin per application. The amount of the composition comprising an acidic buffer and an acid protease administered generally ranges from about 0.001 mg to about 1.0 mg per $cm^2$ skin per application, preferably from about 0.01 mg to about 0.5 mg per $cm^2$, more preferably from about 0.05 to about 0.25 $mg/cm^2$ skin per application, which may vary upon the severity of the condition to be treated, the sensitivity of the subject's skin, the location of the treatment site on the subject, and the efficacy of the compounds employed.

6. EXAMPLES

In order to more fully illustrate the nature of the invention and the manner of practicing the same, the following examples are provided, which are not to be construed as limiting the remainder of the disclosure or the scope of the invention in any way whatsoever.

The following reagents were used in the compositions and methods described in Section 6.1 through 6.4:

AFP 2000, a fungal-derived acid protease, Solvay Inc., Elkhart Ind.; algae extract/aloe extract, Active Organics, Inc., Dallas Tex.; allantoin, Sutton Laboratories, Chatham N.J.; Arlacel 65, ICI Surfactants, Wilmington Del.; aspartic acid, Ajinomoto USA, Inc., Teaneck N.J.; BHT, Eastman Kodak, Co., Rochester N.Y.; butylene glycol, Hoechst Celanese, Co., Charlotte N.C.; Carbomer, B.F. Goodrich, Co., Brecksville Ohio; cetearyl alcohol, Lipo Chemicals, Inc., Patterson N.J.; cetyl alcohol, Lipo Chemicals, Inc., Patterson N.J.; citric acid, Roche Vitamins and Fine Chemicals, Nutley N.J.; Cosmowax, Croda Chemicals, Ltd., Parsippany N.J.; cyclomethicone, Dow Chemicals USA, Midland Mich.; dihydroxyacetone, Rona/E. Merck Industries, Hawthorne N.Y.; dimethicone, Dow Chemicals USA, Midland Mich.; disodium EDTA, Ciba-Geigy Co., Greensboro N.C.; DL-Panthenol, Roche Vitamins and Fine Chemicals, Nutley N.J.; ethoxydiglycol, Gattefosse S.A., Paris, France; gluconic acid, Sigma Chemicals, St. Louis Mo.; Glycereth-26, Amerchol Co., Edison N.J.; glyceral stearate, Croda Chemicals, Ltd., Parsippany N.J.; lactic acid USP 88%, Rita Corporation, Woodstock Ill.; lecithin/asiatic acid, Active Organics, Dallas Tex,; methyl gluceth-20, Amerchol Co., Edison N.J.; methylparaben, Napp Co., Lodi N.J.; octyl palmitate, ICI Surfactants, Wilmington Del.; octyldodecyl neopentanoate, ICI Surfactants, Wilmington Del.; PEG-75, Lipo Chemicals, Inc., Patterson N.J.; PEG-40 stearate, Lipo Chemicals, Inc., Patterson N.J.; Pepsin 1:15, 000 NF, American Laboratories, Inc., Omaha Nebr.; phosphoric acid 85%, Sigma Chemicals, Inc., St. Louis Mo.; polyacrylamide/C13–14 isoparaffin/laureth-7, Seppic, Co., Paris, France; propylene glycol, Dow Chemicals USA, Midland Mich.; propylparaben, Napp Co., Lodi N.J.; retinyl palmitate, Roche Vitamins and Fine Chemicals, Nutley N.J.; salicylic acid, Kalama Co., Seattle Wash.; sodium carboxylmethylcellulose 7HXF, Aqualon, Co., Wilmington Del.; sodium hyaluronate, Active Organics, Dallas Tex.; steareth-10, Lipo Chemicals, Inc., Patterson N.J.; tocopheryl acetate, Roche Vitamins and Fine Chemicals, Nutley N.J.; triethanolamine 99%, BASF Co., Mount Olive N.J.; and xantham gum, Kelco, San Diego, Calif.

6.1 Enhancement of Skin Exfoliation

A composition of the present invention was tested at differing concentrations of the acid protease pepsin, 1:15, 000 NF, American Laboratories, Inc., Omaha, Nebr., and the acidic buffer lactic acid on individual human volar forearms for the enhancement of skin exfoliation and cell renewal. Twenty subjects between the ages of 30 and 60 years were selected and were required to refrain from using any products on their volar forearm, except those supplied in conjunction with the test procedure (which included a synthetic soap) for 5 days before and during the test period. None of the subjects: (1) was pregnant or lactating or intended to become pregnant within three months following the test; (2) had one or more known communicable diseases; (3) was involved in any other clinical study at the time of the test; (4) suffered from psoriasis, dermatitis, and/or eczema; (5) was taking medication considered likely to interfere with the test results, including retinoids, corticosteroids, or antibiotics; (6) had taken retinoids, corticosteroids, or antibiotics during the six months prior to the test; and/or (7) had used tobacco products, had sensitive skin, had a skin type deemed unsuitable for the test, or had other characteristics considered likely to make them unsuitable for the test.

Each volar forearm of each subject was patched with four 2×3 cm adhesive bandages, to which had been applied 1–2 gm/cm$^2$ of 5% ultra-pure dansyl chloride milled into petrolatum. Three of the bandages on each forearm were used as test sites and the remaining one was used as a control.

The four sites on each forearm of each subject were covered with the dansyl chloride-loaded bandages and were left undisturbed for 24 hours. At the end of the 24 hour period, the bandages were removed, the sites washed and staining of the sites by dansyl chloride was confirmed by viewing with a long wave UV light source to detect fluorescence by the dansyl chloride. The six non-control dansyl chloride stained test sites on each subject received twice daily topical applications of 1–2 ml/cm$^2$ of a randomized selection of test compositions described in Table I. Upon application, the test compositions were rubbed into the skin at the test sites until the sites were no longer wet. After the dansyl chloride staining was verified, the test sites and the control sites were left uncovered and were handled in the same manner except that the test sites received the test applications and the control sites did not receive any test composition.

TABLE I

| Test Composition No. | Lactic Acid (100%) % by wt. | Acid Protease[a] % by wt. | HUT units/g * 10$^6$ | Sorbic Acid preservative % by wt. | Deionized Water % by wt. |
|---|---|---|---|---|---|
| 1 | 0.00 | 0.00 | 0.0 | 0.05 | 99.95 |
| 2 | 1.50 | 0.00 | 0.0 | 0.05 | 98.45 |
| 3 | 1.50 | 0.02 | 0.02 | 0.05 | 98.43 |
| 4 | 1.50 | 0.20 | 0.2 | 0.05 | 98.25 |
| 5 | 1.50 | 1.00 | 1.0 | 0.05 | 97.45 |
| 6 | 1.50 | 2.00 | 2.0 | 0.05 | 96.45 |
| 7 | 1.50 | 4.00 | 4.0 | 0.05 | 94.45 |
| 8 | 3.00 | 0.00 | 0.0 | 0.05 | 96.95 |
| 9 | 3.00 | 0.02 | 0.02 | 0.05 | 96.93 |
| 10 | 3.00 | 0.20 | 0.2 | 0.05 | 96.75 |
| 11 | 3.00 | 1.00 | 1.0 | 0.05 | 95.95 |
| 12 | 3.00 | 2.00 | 2.0 | 0.05 | 94.95 |
| 13 | 3.00 | 4.00 | 4.0 | 0.05 | 92.95 |

[a]The acid protease employed was Pepsin, 1:15,000, NF, American Laboratories, Inc., Omaha NE.

Exfoliation/keratolysis of the stratum corneum was determined by visualizing the dansyl chloride stains daily under a long wave UV light source to measure stain removal. The percent increase in exfoliation/keratolysis and accompanying cell renewal of the stratum corneum was calculated by the following formula:

$$\% \text{ Increase} = \frac{(\text{days for removal of untreated area} - \text{days for removal of treated area})}{\text{days for removal of untreated area}} \times 100$$

TABLE II

| Test Composition No. | Lactic Acid Conc. (%) | Acid Protease[a] Conc. (%) | HUT units/g * 10$^6$ | Effect of Composition (% Increase over Control Value) | Pepsin Effect (% Increase over Lactic Acid Control Values) |
|---|---|---|---|---|---|
| 1 | 0.00 | 0.00 | 0.0 | 0 (Control) | 0 |
| 2 | 1.50 | 0.00 | 0.0 | 14 | 0 (Control) |
| 3 | 1.50 | 0.02 | 0.02 | 14 | 0 |
| 4 | 1.50 | 0.20 | 0.2 | 17 | 21 |
| 5 | 1.50 | 1.00 | 1.0 | 25 | 79 |
| 6 | 1.50 | 2.00 | 2.0 | 28 | 100 |
| 7 | 1.50 | 4.00 | 4.0 | 33 | 136 |
| 8 | 3.00 | 0.00 | 0.0 | 18 | 0 (Control) |
| 9 | 3.00 | 0.02 | 0.02 | 18 | 0 |
| 10 | 3.00 | 0.20 | 0.2 | 23 | 28 |
| 11 | 3.00 | 1.00 | 1.0 | 31 | 72 |
| 12 | 3.00 | 2.00 | 2.0 | 33 | 83 |
| 13 | 3.00 | 4.00 | 4.0 | 36 | 100 |

[a]The acid protease employed was Pepsin, 1:15,000, NF, American Laboratories, Inc., Omaha NE.

Figure 2:
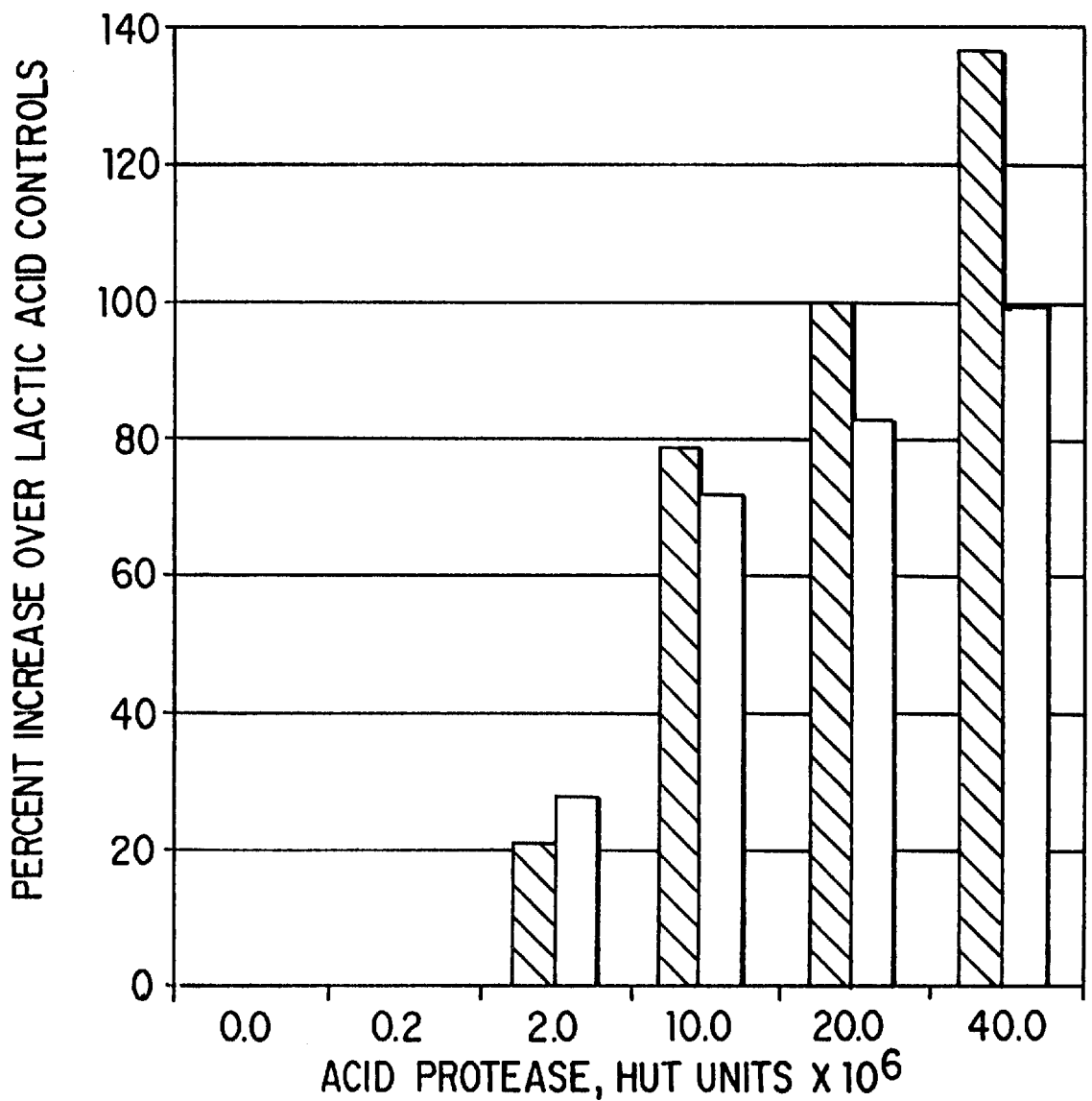
FIG. 2 is a bar graph demonstrating the percent increases in exfoliation/cell renewal rates given by various concentrations of an acid protease (pepsin) over that of an acidic buffer alone (lactic acid) at concentrations of 1.5% and 3.0%. ▧ 1.5% lactic acid, □ 3.0% lactic acid.

The data collected from the test are summarized in Table II and in FIGS. 1 and 2. As seen in Table II, column 5, the acidic buffer lactic acid had some positive keratolytic/cell renewal effects alone [compare test composition 2 and 8 to the control (test composition 1)] at concentrations of 1.5% and 3.0% by weight. These positive keratolytic/cell renewal effects are significantly enhanced in the presence of the acid protease pepsin, (see test compositions 3–7 and 9–13). It is also apparent that the enhancements are dose dependent, i.e., stratum corneum exfoliation/cell renewal rates increase as the concentration of the acid protease increases, see column 5 of Table II. FIG. 1 presents the data in column 5 graphically.

Column 6 of Table II reflects the percent increase in exfoliation/cell renewal rates given by various concentrations of the acid protease pepsin over that given by lactic acid alone at 1.5% and 3.0% by weight concentration. The data in column 6 is presented graphically in FIG. 2. It is apparent that, although the acid protease effect is significant at both lactic acid concentrations employed, the greater percent enhancements are given by the acid protease pepsin at a lactic acid concentration of 1.5% by weight.

A low level of redness and swelling was observed on the skin of some of the test subjects, approximately 75% of the skin test sites at a 3% by weight lactic acid concentration, but very little was observed at a 1.5% by weight lactic acid concentration. Furthermore, this finding was largely independent of the presence of pepsin. Thus, significant exfoliation/cell renewal is accomplished by employing an acidic buffer at a low, non-irritating level in the presence of an appropriate concentration of an acid protease. In contrast to proteases which are active in the physiological pH range, acid proteases, as defined herein, applied to the skin maintain their proteolytic activity only until the skin's own natural processes raise the pH of the skin's surface to its normal value of approximately 5.5.

6.2 Compositions for Use in the Methods of the Present Invention

The following Tables recite formulations of different examples of compositions of the present invention. All of the following compositions were adjusted to a pH of about 3.0 to 3.2 with, for example, dilute phosphoric acid or sodium hydroxide, NaOH.

TABLE III

WASH AP-01

| | PERCENT BY WEIGHT |
|---|---|
| ASPARTIC ACID | 1.50 |
| DEIONIZED WATER | 82.50 |
| METHYLPARABEN | 0.20 |
| PEG 75 | 1.50 |
| DISODIUM EDTA | 0.05 |
| ALLANTOIN | 0.25 |
| GLYCERETH 26 | 1.00 |
| ETHOXYDIGLYCOL | 4.00 |
| PROPYLENE GLYCOL | 4.00 |
| AFP 2000 | 5.00 |
| TOTALS | 100.00 |

TABLE IV

WASH AP-02

| | PERCENT BY WEIGHT |
|---|---|
| PHOSPHORIC ACID 85% | 1.20 |
| DEIONIZED WATER | 86.80 |
| METHYLPARABEN | 0.20 |
| PEG 75 | 1.50 |
| DISODIUM EDTA | 0.05 |
| ALLANTOIN | 0.25 |
| GLYCERETH 26 | 1.00 |
| ETHOXYDIGLYCOL | 4.00 |
| PROPYLENE GLYCOL | 4.00 |
| PEPSIN 1,000 HUT UNITS/MG | 1.00 |
| TOTALS | 100.00 |

TABLE V

Serum AP-03

| | PERCENT BY WEIGHT |
|---|---|
| SALICYLIC ACID | 0.50 |
| TRIETHANOLAMINE 99% | 1.00 |
| LACTIC ACID USP 88% | 1.20 |
| DEIONIZED WATER | 82.70 |
| SODIUM CARBOXY-METHYCELLULOSE 7HXF | 0.60 |
| METHYLPARABEN | 0.20 |
| PEG 75 | 1.50 |
| DISODIUM EDTA | 0.05 |
| ALLANTOIN | 0.25 |
| METHYL GLUCETH-20 | 1.00 |
| GLYCERETH 26 | 1.00 |
| ETHOXYDIGLYCOL | 4.00 |
| PROPYLENE GLYCOL | 4.00 |
| LECITHIN/ASIATIC ACID | 1.00 |
| PEPSIN 1,000 HUT UNITS/MG | 1.00 |
| TOTALS | 100.00 |

TABLE VI

Serum AP-04

| | PERCENT BY WEIGHT |
|---|---|
| GLUCONIC ACID | 1.50 |
| DEIONIZED WATER | 84.08 |
| METHYLPARABEN | 0.02 |
| SODIUM CARBOXY-METHYCELLULOSE 7HXF | 0.60 |
| PEG 75 | 1.50 |
| DISODIUM EDTA | 0.05 |
| ALLANTOIN | 0.25 |
| METHYL GLUCETH-20 | 1.00 |
| GLYCERETH 26 | 1.00 |
| ETHOXYDIGLYCOL | 4.00 |
| PROPYLENE GLYCOL | 4.00 |
| LECITHIN/ASIATIC ACID | 1.00 |
| PEPSIN 1,000 HUT UNITS/MG | 1.00 |
| TOTALS | 100.00 |

TABLE VII

Pepsin Lotion AP-05

| | PERCENT BY WEIGHT |
|---|---|
| DEIONIZED WATER | 64.75 |
| XANTHAN GUM | 0.10 |
| DISODIUM EDTA | 0.10 |
| ALLANTOIN | 0.50 |
| ALGAE EXTRACT (and) ALOE EXTRACT | 6.00 |
| METHYLPARABEN | 0.20 |
| DL-PANTHENOL | 0.50 |
| ETHOXYDIGYCOL | 4.00 |
| BUTYLENE GYCOL | 5.00 |
| CETYL ALCOHOL | 2.00 |
| GLYCERYL STEARATE | 2.00 |
| OCTYL PALMITATE | 4.00 |
| CYCLOMETHICONE | 2.00 |
| PROPYLPARABEN | 0.10 |
| BHT | 0.05 |
| POLYACRYLAMIDE (and) C 13–14 ISOPARAFFIN (and) LAURETH-7 | 1.50 |
| SODIUM HYALURONATE | 3.00 |
| RETINYL PALMITATE | 0.10 |
| TOCOPHERYL ACETATE | 0.10 |
| PEPSIN 1,000 HUT UNITS/MG | 1.00 |
| CITRIC ACID | 3.00 |
| TOTALS | 100.00 |

TABLE VIII

Renewal Gel AP-06

| | PERCENT BY WEIGHT |
|---|---|
| DEIONIZED WATER | 89.60 |
| CARBOMER | 1.50 |
| SALICYLIC ACID | 0.50 |
| LACTIC ACID USP 88% | 1.20 |
| PROPYLENE GLYCOL | 6.00 |
| PEPSIN 1,000 HUT UNITS/MG | 1.00 |
| METHYLPARABEN | 0.15 |
| PROPYLPARABEN | 0.05 |
| TOTALS | 100.00 |

TABLE IX

Renewal Gel AP-07

| | PERCENT BY WEIGHT |
|---|---|
| DEIONIZED WATER | 85.10 |
| POLYACRYLAMIDE (and) C13–14 | 4.00 |

TABLE IX-continued

Renewal Gel AP-07

| | PERCENT BY WEIGHT |
|---|---|
| ISOPARAFFIN (and) LAURETH-7 | |
| SALICYLIC ACID | 0.50 |
| LACTIC ACID USP 88% | 1.20 |
| BUTYLENE GLYCOL | 8.00 |
| PEPSIN 1,000 HUT UNITS/MG | 1.00 |
| METHYLPARABEN | 0.15 |
| PROPYLPARABEN | 0.05 |
| TOTALS | 100.00 |

TABLE X

Self-Tanning Lotion AP-08

| | PERCENT BY WEIGHT |
|---|---|
| DEIONIZED WATER | 48.15 |
| XANTHAN GUM | 0.75 |
| PROPYLENE GLYCOL | 5.00 |
| METHYLPARABEN | 0.20 |
| PROPYLPARABEN | 0.10 |
| PEPSIN 1,000 HUT UNITS/MG | 2.00 |
| STEARETH-10 | 0.70 |
| ARLACEL 1651 | 1.20 |
| PEG-40 STEARATE | 0.40 |
| COSMOWAX J2 | 1.00 |
| CETEARYL ALCOHOL | 1.50 |
| CYCLOMETHICONE | 5.00 |
| DIMETHICONE | 0.50 |
| OCTYLDODECYL NEOPENTANOATE | 28.50 |
| DIHYDROXYACETONE | 5.00 |
| TOTALS | 100.00 |

6.3 Stabilization Composition

The following composition at pH 3.0 retains at least 90% of its acid protease activity over a period of at least three months, during which the composition was stored at 37° C.

| | % by weight |
|---|---|
| Cyclomethicone | 5.0 |
| Cetyl Alcohol | 1.5 |
| Arlacel 165 | 1.5 |
| Dimethicone | 1.0 |
| Sepigel 305 | 3.0 |
| Phenoxyethanol | 1.0 |
| EDTA, disodium | 0.1 |
| Butylene Glycol | 10.0 |
| Citric acid/Sodium Citrate | 3.0 |
| Lactic acid (100%) | 1.5 |
| Sorbic acid | 0.05 |
| Lactose | 1.0 |
| Pepsin; 1000 HUT Units/mg | 1.0 |
| $H_2O$ | 70.35 |

6.4 Proteolytic Activity at Varying pH Levels

Two acid protease enzymes were tested over a range of pH values to determine if they have proteolytic activity at a pH less than about pH 5.5 and whether the activity decreases to less than about 10% compared to its activity at the pH optimum. Proteolytic activity was measured by determining the proteolytic effect on hemoglobin using the HUT assay as described below. The two acid proteases were pepsin 1:15, 000 NF, at about 1000 HUT units/mg, supplied by American Laboratories, Inc., Omaha Nebr., and AFP 2000, a fungally-derived acid protease supplied by Solvay, Inc., Elkhart Ind., at about 100 HUT units/mg. The assay was performed first by preparing stock solutions HEMOGLOBIN SUBSTRATE and TCA STOCK. The hemoglobin substrate was made by dissolving 2 g of bovine hemoglobin, Sigma Chemicals, Inc., St. Louis Mo., into 80 ml distilled water. This solution was then titrated to the correct pH, either, pH 2, 3.5, 5.5 or 6.0. For pH values between 1 and 3, 1.8 g of phosphoric acid was dissolved for a final concentration of 100 mM and the pH was adjusted with 50% sodium hydroxide or 50% hydrochloric acid. For pH values between 3 and 6, 2 g of citric acid was dissolved for a final concentration of 100 mM and the pH was adjusted with 50% sodium hydroxide or hydrochloric acid. The solutions were brought to a final volume of 100 ml by adding distilled water. The substrates with differing pH values were then incubated at 30° C. for 20 minutes and subsequently filtered through glass wool. The TCA stock solution was prepared by dissolving 5 g of trichloroacetic acid into 100 ml distilled water.

The enzyme standards were then prepared by dissolving 10 mg of pepsin in 10 ml distilled water and by dissolving 100 mg of AFP 2000 and 300 mg citric acid in 8 ml distilled water. This solution was then adjusted to a pH of about 3.5 with 6M HCl of 50% sodium hydroxide and the final volume was brought to 10 ml by the addition of distilled water.

For each of the samples, four tubes were marked, "B", "T1", "T2" and "T3", and 4 ml of the hemoglobin substrate solution was added to each tube, which were then placed at 37° C. 100 μl of the enzyme standard was added to each "T" labeled tube, i.e., T1, T2 and T3. The tubes were then incubated for 20 minutes at 37° C. for pepsin and 30 minutes for AFP 2000. 10 ml of the TCA stock solution was then added to all the tubes, and 100 μl of enzyme was added to tube "B". The tubes were then centrifuged for one minute at 1000 rpm. The sample is each tube was filtered through a syringe filter into a quartz cuvette and the absorbance at 280 nm was taken. The background absorbance was deducted from each of the "T"'s absorbance and the individual "T1", "T2" and "T3" absorbencies were averaged for each enzyme at each pH tested.

Figure 3:
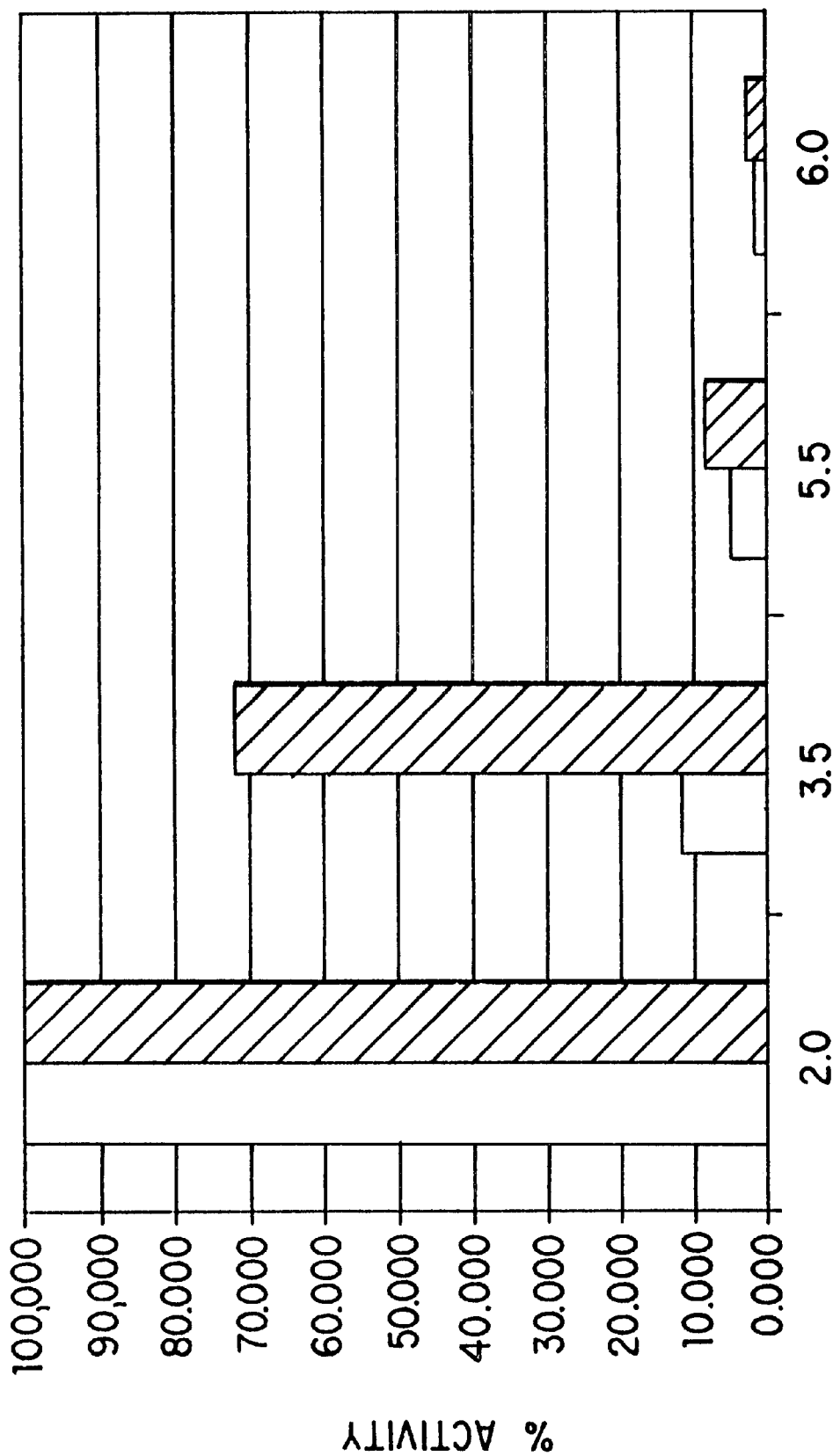
FIG. 3 is a bar graph demonstrating the difference in activity of pepsin and AFP 2000, Solvay, Inc., Elkhart Ind., a fungally-derived acid protease, at varying pH levels in the HUT assay. □ AFP 2000, ▧ pepsin.

FIG. 3 demonstrates that both of the enzymes were optimally active at pH 2.0. Further, both enzymes had less than 10% activity at pH 5.5 and greater as compared to the optimal level at pH 2.0. This assay clearly demonstrates that these enzymes are enzymes which can be used in the present invention. Further, by using such an assay, it may be determined which additional enzymes are suitable for use in the present invention.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A composition comprising: (1) an acid protease which is enzymatically active below about pH 5.5 and which is significantly inactive at or above pH 5.5; and (2) an acidic buffer comprising an inorganic acid which, when applied to skin, temporarily lowers the surface pH of the skin to below about pH 5.5, the acidic buffer being subject to neutralization by natural epidermal processes, such that the surface pH of the skin, to which such acidic buffer was applied, returns to about pH 5.5.

2. The composition according to claim 1 wherein the acidic buffer further comprises a pharmaceutically or cosmetically acceptable carrier, vehicle or excipient.

3. The composition according to claim 2 wherein the pharmaceutically or cosmetically acceptable carrier, vehicle or excipient component of the acidic buffer is selected from the group consisting of lotions, tinctures, creams, emulsions, gels, ointments, water, water-workable cream, polyvinyl alcohol, hydroxyethyl cellulose, cellulose, hydrophilic acrylic polymer, emollients, skin moisturizing components, enzyme stabilizers, glycerol, surfactants, preservatives, hydrophilic thickening agents used in pharmaceutical formulations and mixtures thereof.

4. The composition according to claim 1 wherein the acid protease is selected from the group consisting of fungal proteases, bacterial proteases or mammalian proteases or mixtures thereof.

5. The composition according to claim 4 wherein the acid protease is selected from the group consisting of pepsin, cathepsin, human urinary acid protease, rhizopuspepsin, penicillopepsin, endothiapepsin or mixtures thereof.

6. The composition according to claim 1 wherein the inorganic acid is selected from the group consisting of phosphoric acid, pyrophosphoric acid, triphosphoric acid, polyphosphoric acid, sodium bisulfate, potassium bisulfate or mixtures thereof.

7. The composition according to claim 1 wherein the acid protease is present in an amount of about 0.001% to about 75.0% by weight of the final composition.

8. The composition according to claim 7 wherein the acid protease is present in an amount of about 0.1% to about 50.0% by weight of the final composition.

9. The composition according to claim 8 wherein the acid protease is present in an amount of about 1.0% to about 5.0% by weight of the final composition.

10. The composition according to claim 1 wherein the acid protease has a total specific activity of about 1.0 to about 5000 HUT units/mg.

11. The composition according to claim 10 wherein the acid protease has a total specific activity of about 50.0 to about 3000 HUT units/mg.

12. The composition according to claim 11 wherein the acid protease has a total specific activity of about 500 to about 1500 HUT units/mg.

13. The composition according to claim 1 wherein the acid component of the acidic buffer is present in an amount of about 0.001% to about 95.0% by weight of the final composition.

14. The composition according to claim 13 wherein the acid component of the acidic buffer is present in an amount of about 0.01% to about 25.0% by weight of the final composition.

15. The composition according to claim 14 wherein the acid component of the acidic buffer is present in an amount of about 1.0% to about 5.0% by weight of the final composition.

16. A method for enhancing epidermal exfoliation or for enhancing epidermal cell renewal which comprises topically administering to a subject on an area of skin an effective amount of a composition comprising (1) an acid protease which is enzymatically active below about pH 5.5 and which is significantly inactive at or above pH 5.5; and (2) an acidic buffer which, when applied to skin, temporarily lowers the surface pH of the skin to below about pH 5.5 for a period of time effective for enhancing epidermal exfoliation or epidermal cell renewal, the acidic buffer being subject to neutralization by natural epidermal processes, such that the surface pH of the skin, to which such acidic buffer was applied, returns to about 5.5.

17. The method according to claim 16 wherein the acidic buffer further comprises a pharmaceutically or cosmetically acceptable carrier, vehicle or excipient.

18. The method according to claim 17 wherein the pharmaceutically or cosmetically acceptable carrier, vehicle or excipient component of the acidic buffer is selected from the group consisting of lotions, tinctures, creams, emulsions, gels, ointments, water, water-workable cream, polyvinyl alcohol, hydroxyethyl cellulose, cellulose, hydrophilic acrylic polymer, emollients, skin moisturizing components, enzyme stabilizers, glycerol, surfactants, preservatives, hydrophilic thickening agents used in pharmaceutical formulations and mixtures thereof.

19. The method according to claim 16 wherein the acid protease is selected from the group consisting of fungal proteases, bacterial proteases or mammalian proteases or mixtures thereof.

20. The method according to claim 19 wherein the acid protease is selected from the group consisting of pepsin, cathepsin, human urinary acid protease, rhizopuspepsin, penicillopepsin, endothiapepsin or mixtures thereof.

21. The method according to claim 16 wherein the acid protease is pepsin.

22. The method according to claim 16 wherein the acid component of the acidic buffer is selected from the group consisting of inorganic acids, organic acids or mixtures thereof.

23. The method according to claim 22 wherein the inorganic acid is selected from the group consisting of phosphoric acid, pyrophosphoric acid, triphosphoric acid, polyphosphoric acid, sodium bisulfate, potassium bisulfate or mixtures thereof.

24. The method according to claim 22 wherein the organic acid is selected from the group consisting of lactic acid, citric acid, sorbic acid, glycolic acid, malic acid, gluconic acid or mixtures thereof.

25. The method according to claim 16 wherein the acid protease is present in an amount of about 0.001% to about 75.0% by weight of the final composition.

26. The method according to claim 25 wherein the acid protease is present in an amount of about 0.1% to about 50.0% by weight of the final composition.

27. The method according to claim 26 wherein the acid protease is present in an amount of about 1.0% to about 5.0% by weight of the final composition.

28. The method according to claim 16 wherein the acid protease has a total specific activity of about 1.0 to about 5000 HUT units/mg.

29. The method according to claim 28 wherein the acid protease has a total specific activity of about 50.0 to about 3000 HUT units/mg.

30. The method according to claim 29 wherein the acid protease has a total specific activity of about 500 to about 1500 HUT units/mg.

31. The method according to claim 16 wherein the acid component of the acidic buffer is present in an amount of about 0.001% to about 95.0% by weight of the final composition.

32. The method according to claim 31 wherein the acid component of the acidic buffer is present in an amount of about 0.01% to about 25.0% by weight of the final composition.

33. The method according to claim 32 wherein the acid component of the acidic buffer is present in an amount of about 1.0% to about 5.0% by weight of the final composition.

34. The method according to claim 16 wherein the surface pH of the skin is below about pH 5.5 for about 5 minutes to about 4 hours.

35. The method according to claim 34 wherein the surface pH of the skin is below about pH 5.5 for about 30 minutes to about 2 hours.

36. The method according to claim 35 wherein the surface pH of the skin is below about pH 5.5 for about 30 minutes to about 1 hour.

37. A method for enhancing epidermal exfoliation or for enhancing epidermal cell renewal which comprises topically administering to a subject on an area of skin an effective amount of a composition comprising (1) an acid protease which is enzymatically active below about pH 5.5 and which is significantly inactive at or above pH 5.5 present in an amount of 4% by weight of the final composition having an activity of 4000 HUT units/mg; and (2) an acidic buffer comprising lactic acid present in an amount of 3.0% by weight of the final composition which when applied to skin temporarily lowers the surface pH of the skin to below about pH 5.5 for a period of time effective for enhancing epidermal exfoliation or epidermal cell renewal, the acidic buffer being subject to neutralization by natural epidermal processes, such that the surface pH of the skin, to which such acidic buffer was applied, returns to about pH 5.5.

38. The method according to claim 37 in which the acid protease is pepsin.

39. A method for enhancing epidermal exfoliation or for enhancing epidermal cell renewal which comprises topically administering to a subject on an area of skin an effective amount of a composition comprising (1) an acid protease which is enzymatically active below about pH 5.5 and which is significantly inactive at or above pH 5.5 present in an amount of 4% by weight of the final composition having an activity of 4000 HUT units/mg; and (2) an acidic buffer comprising lactic acid present in an amount of 1.5% by weight of the final composition which when applied to skin temporarily lowers the surface pH of the skin to below about pH 5.5 for a period of time effective for enhancing epidermal exfoliation or epidermal cell renewal, the acidic buffer being subject to neutralization by natural epidermal processes, such that the surface pH of the skin, to which such acidic buffer was applied, returns to about pH 5.5.

40. The method according to claim 39 in which the increase in exfoliation is 136% as compared to control.

41. The method according to claim 39 in which the acid protease is pepsin.

* * * * *